(12) United States Patent
Demarest et al.

(10) Patent No.: US 10,870,014 B2
(45) Date of Patent: Dec. 22, 2020

(54) ORAL TREATMENT DEVICE

(71) Applicant: COLGATE-PALMOLIVE COMPANY, New York, NY (US)

(72) Inventors: Scott Demarest, Basking Ridge, NJ (US); Francis Tatu, Manlius, NY (US); Mark Bartlett, North East, PA (US)

(73) Assignee: Colgate-Palmolive Company, New York, NY (US)

( * ) Notice: Subject to any disclaimer, the term of this patent is extended or adjusted under 35 U.S.C. 154(b) by 613 days.

(21) Appl. No.: 14/979,014

(22) Filed: Dec. 22, 2015

(65) Prior Publication Data
US 2017/0173353 A1 Jun. 22, 2017

(51) Int. Cl.
*A61N 5/06* (2006.01)
*A61C 19/06* (2006.01)

(52) U.S. Cl.
CPC .......... *A61N 5/0603* (2013.01); *A61C 19/063* (2013.01); *A61C 19/066* (2013.01); *A61N 5/062* (2013.01); *A61N 2005/0606* (2013.01)

(58) Field of Classification Search
CPC .................. A61N 5/0603; A61N 5/062; A61N 2005/0606; A61C 5/14; A61C 19/066; A61C 19/06; A61C 19/063; A61C 9/0006; A61C 9/0013
USPC ......... 433/6, 215, 41, 43; 602/902; 128/859, 128/862, 848, 861
See application file for complete search history.

(56) References Cited

U.S. PATENT DOCUMENTS

| | | | |
|---|---|---|---|
| 5,316,473 | A | 5/1994 | Hare |
| 5,487,662 | A | 1/1996 | Kipke et al. |
| 6,616,447 | B1 | 9/2003 | Rizoiu et al. |
| 6,650,018 | B1 | 11/2003 | Zhao et al. |
| 6,893,259 | B1 | 5/2005 | Reizenson |
| 6,976,841 | B1 | 12/2005 | Osterwalder |

(Continued)

FOREIGN PATENT DOCUMENTS

| | | |
|---|---|---|
| CN | 102188294 | 9/2011 |
| DE | 202011104169 | 10/2011 |

(Continued)

OTHER PUBLICATIONS

Merriam-Webster, "gap", https://www.merriam-webster.com/dictionary/gap , 2019.*

(Continued)

*Primary Examiner* — Heidi M Eide
*Assistant Examiner* — Drew S Folgmann

(57) ABSTRACT

An oral treatment device that includes a mouthpiece and an electromagnetic radiation source. In one aspect, the oral treatment device includes a mouthpiece comprising a curved wall having a concave inner surface and a bite platform extending from the concave inner surface of the curved wall to a distal end, the distal end of the bite platform extending continuously in a non-interrupted manner from a first end of the bite platform to a second end of the bite platform; an electromagnetic radiation source configured to emit electromagnetic radiation from the curved wall; and wherein the bite platform comprises a collapsible region such that the mouthpiece is alterable between: (1) a biased state in which the curved wall has a first curvature; and (2) a flexed state in which the curved wall has a second curvature that is different than the first curvature.

4 Claims, 9 Drawing Sheets

(56) References Cited

U.S. PATENT DOCUMENTS

| | | | |
|---|---|---|---|
| 7,086,862 B2 | 8/2006 | Craig | |
| 7,156,656 B2 | 1/2007 | Duret | |
| 7,331,784 B2 | 2/2008 | Suzuki | |
| 7,572,124 B2 | 8/2009 | Cipolla et al. | |
| 7,645,137 B2 | 1/2010 | Wasyluch | |
| 7,802,988 B2 | 9/2010 | Yarborough | |
| 8,172,570 B2 | 5/2012 | Baughman | |
| 8,215,954 B2 | 7/2012 | Levine | |
| 8,241,035 B2 | 8/2012 | Jones et al. | |
| 8,371,853 B2 | 2/2013 | Levine | |
| 8,591,227 B2 | 11/2013 | Levine | |
| 8,602,774 B2 | 12/2013 | Wasyluch | |
| 8,754,426 B2 | 6/2014 | Marx et al. | |
| 9,299,887 B2 | 3/2016 | Lowenthal et al. | |
| 9,492,257 B2 | 11/2016 | Jablow et al. | |
| 9,539,075 B2 | 1/2017 | Sanders | |
| 9,636,198 B2 | 5/2017 | Kodama | |
| 9,730,780 B2 | 8/2017 | Brawn et al. | |
| 9,780,270 B2 | 10/2017 | Kahrs et al. | |
| 9,889,315 B2 | 2/2018 | Demarest et al. | |
| 9,901,744 B2 | 2/2018 | Demarest et al. | |
| 9,913,992 B2 | 3/2018 | Demarest et al. | |
| 9,968,422 B2 | 5/2018 | Valoir | |
| 9,974,630 B2 | 5/2018 | Heacock et al. | |
| 2005/0048444 A1 | 3/2005 | Creamer | |
| 2005/0153256 A1* | 7/2005 | Livolsi | A61C 9/0006 433/37 |
| 2005/0186539 A1* | 8/2005 | McLean | A61C 19/063 433/215 |
| 2005/0202363 A1 | 9/2005 | Osterwalder | |
| 2005/0244792 A1 | 11/2005 | Verdi et al. | |
| 2005/0266370 A1 | 12/2005 | Suzuki | |
| 2006/0003284 A1 | 1/2006 | Sale et al. | |
| 2006/0019214 A1 | 1/2006 | Lawrence et al. | |
| 2006/0039874 A1 | 2/2006 | Wong | |
| 2006/0141422 A1 | 6/2006 | Philp, Jr. et al. | |
| 2006/0172260 A1* | 8/2006 | Allred | A61C 19/066 433/215 |
| 2006/0201520 A1 | 9/2006 | Christensen, III | |
| 2007/0003905 A1 | 1/2007 | Nguyen et al. | |
| 2007/0054233 A1 | 3/2007 | Rizoiu et al. | |
| 2008/0032253 A1 | 2/2008 | Montgomery et al. | |
| 2008/0050693 A1* | 2/2008 | Fischer | A61C 19/063 433/25 |
| 2008/0063999 A1 | 3/2008 | Osborn | |
| 2008/0233541 A1 | 9/2008 | De Vreese et al. | |
| 2009/0017422 A1 | 1/2009 | Creamer | |
| 2009/0155740 A1 | 6/2009 | Jensen et al. | |
| 2010/0311007 A1 | 12/2010 | Eliyahov | |
| 2011/0076636 A1 | 3/2011 | Wolff et al. | |
| 2012/0214122 A1* | 8/2012 | Dwyer | A61C 19/066 433/29 |
| 2012/0295212 A1 | 11/2012 | Sakimura et al. | |
| 2013/0029291 A1 | 1/2013 | Williams | |
| 2013/0045457 A1 | 2/2013 | Chetiar et al. | |
| 2013/0052613 A1 | 2/2013 | Chetiar et al. | |
| 2013/0175515 A1 | 7/2013 | Ray et al. | |
| 2013/0280671 A1 | 10/2013 | Brawn et al. | |
| 2014/0186789 A1 | 7/2014 | Valoir | |
| 2014/0272770 A1 | 9/2014 | Hurley | |
| 2015/0004556 A1 | 1/2015 | Jin et al. | |
| 2015/0044628 A1 | 2/2015 | Flyash | |
| 2015/0132709 A1 | 5/2015 | Park et al. | |
| 2015/0204490 A1 | 7/2015 | Zheng et al. | |
| 2015/0360606 A1 | 12/2015 | Thompson et al. | |
| 2016/0035924 A1 | 2/2016 | Oraw et al. | |
| 2016/0271415 A1 | 9/2016 | Min | |
| 2016/0331487 A1 | 11/2016 | Newman et al. | |
| 2017/0080249 A1 | 3/2017 | Brawn et al. | |
| 2017/0172717 A1 | 6/2017 | Chen et al. | |
| 2017/0189149 A1 | 7/2017 | Golub et al. | |

FOREIGN PATENT DOCUMENTS

| | | |
|---|---|---|
| EP | 1741407 | 1/2007 |
| EP | 1054642 | 5/2008 |
| EP | 2386264 | 11/2011 |
| KR | 100773379 | 11/2007 |
| KR | 101525123 | 6/2015 |
| RU | 2352321 | 4/2009 |
| WO | 2005/107637 | 11/2005 |
| WO | WO2006020128 | 2/2006 |
| WO | 2010/098764 | 9/2010 |
| WO | WO2010098761 | 9/2010 |
| WO | 2011/152585 | 12/2011 |
| WO | WO2011159522 | 12/2011 |
| WO | WO2011163220 | 12/2011 |
| WO | WO2013093743 | 6/2013 |
| WO | 2013/155366 | 10/2013 |

OTHER PUBLICATIONS

International Search Report and Written Opinion of the International Searching Authority in International Application No. PCT/US2016/067564, dated Mar. 16, 2017.

Barolet, "Light-Emitting Diodes (LEDs) in Dermatology," Semin Cutan Med Surg. 2008; 27: 227-238.

Belikov et al., "Study of the dynamics of the absorption spectra of human tooth enamel and dentine under heating and ablation by submillisecond pulse radiation of an erbium laser with a generation wavelength of 2.79um," Optics and Spectroscopy, 2010, 109(2):211-216.

Brodbelt et al., "Translucency of Human dental enamel," J Dent. Res. 1981, 60: 1749-1753.

De Moor et al., "The Use of the KTP Laser, an Added Value for Tooth Bleaching," J Oral Laser Applications, 2009, 9: 219-226.

Elliott, "Teeth Whitening, spot zapping, hair taming and even wrinkle erasing: so could BLUE technology be the future of beauty?" May 31, 2015, published online at http://www.dailymail.co.uk/femail/article-3099582/Teeth-whitening-spot-zapping-hair-taming-wrinkle-erasing-BLUE-technology-future-beauty.html.

Hirmer et al., "Spectroscopic study of human teeth and blood from visible to terahertz frequencies for clinical diagnosis of dental pulp vitality," J Infrared Mill Terahz Waves, 2012, 33:366-375.

Joiner et al., "Tooth colour: a review of the literature," J of Dentistry, 2003, 32: 3-12.

Spitzer et al., "The absorption and scattering of light in bovine and human dental enamel," Calcif. Tiss. Res. 1975, 17:129-137.

Bosch et al., "Optical properties of dentin," Chapter 3, Dentine and dentine reactions in the oral cavity, pp. 34-40, 1987.

Young et al., "A study of hydrogen peroxide chemistry and photochemistry in tea stain solution with relevance to clinical tooth whitening," J of Dentistry, 2012, Article in Press.

International Search Report and Written Opinion of the International Searching Authority in International Application No. PCT/US2016/067573, dated Jul. 13, 2017.

Partial International Search Report issued in International Application PCT/US2016/067573 dated Mar. 22, 2017.

* cited by examiner

ORAL TREATMENT DEVICE

BACKGROUND

Tooth whitening is an increasingly popular treatment and dentists and patients alike are searching for techniques that are both convenient and comfortable. Typically, to whiten a user's teeth a composition containing hydrogen peroxide is applied to the teeth and allowed to remain in contact with the teeth to be bleached for a period of time. Current devices are available that allow a user to apply radiation or light to the surfaces of the teeth that are pre-coated with the whitening composition to enhance the effectiveness of the whitening composition. However, currently available devices are bulky and rigid and undesirable for one or more reasons. Specifically, current devices do not emit radiation or light onto the user's pre-coated teeth uniformly and in a manner that effectively covers the entire tooth surface. Furthermore, the rigidity of such devices does not permit the device to be comfortably inserted into a user's mouth and to maintain a consistent distance between the source of radiation or light and the teeth. Thus, a need exists for a tooth whitening device that is able to effectively and consistently emit radiation or light onto a user's teeth.

BRIEF SUMMARY

The present invention may be directed, in one aspect, to an oral treatment device that emits electromagnetic radiation onto surfaces of the user's teeth. The device may include a mouthpiece having a curved wall and a bite platform extending from the curved wall to a distal end. The distal end of the bite platform may extend continuously in a non-interrupted manner such that it does not include any notches therein. The bite platform may include a collapsible region that permits the mouthpiece to be alterable between a biased state and a flexed state, thereby changing the curvature of the mouthpiece to better fit into a particular user's mouth.

In one aspect, an oral treatment device may include a mouthpiece comprising a curved wall having a concave inner surface and a bite platform having an upper surface and a lower surface extending from the concave inner surface of the curved wall to a distal end, the distal end of the bite platform extending continuously in a non-interrupted manner from a first end of the bite platform to a second end of the bite platform; an electromagnetic radiation source configured to emit electromagnetic radiation from the curved wall; and wherein the bite platform comprises a collapsible region such that the mouthpiece is alterable between: (1) a biased state in which the curved wall has a first curvature; and (2) a flexed state in which the curved wall has a second curvature that is different than the first curvature.

In another aspect, the oral treatment device may include a mouthpiece comprising a curved wall having a concave inner surface and a bite platform having an upper surface and a lower surface extending from the concave inner surface of the curved wall to a distal end; an electromagnetic radiation source configured to emit electromagnetic radiation from the curved wall; and wherein the bite platform comprises at least one non-collapsible region and at least one collapsible region, the upper and lower surfaces of the bite platform being substantially flat in the at least one non-collapsible region and the upper and lower surfaces of the bite platform undulating in the at least one collapsible region.

In yet another aspect, the oral treatment device may include a mouthpiece comprising a curved wall having a concave inner surface and a bite platform having an upper surface and a lower surface extending from the concave inner surface of the curved wall to a distal end; an electromagnetic radiation source configured to emit electromagnetic radiation from the curved wall; and wherein the bite platform comprises at least one non-collapsible region and at least one collapsible region, the bite platform having a first thickness measured between the upper and lower surfaces of the bite platform in the at least one non-collapsible region and a second thickness measured between the upper and lower surfaces of the bite platform in the at least one collapsible region, the second thickness being less than the first thickness.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1A:
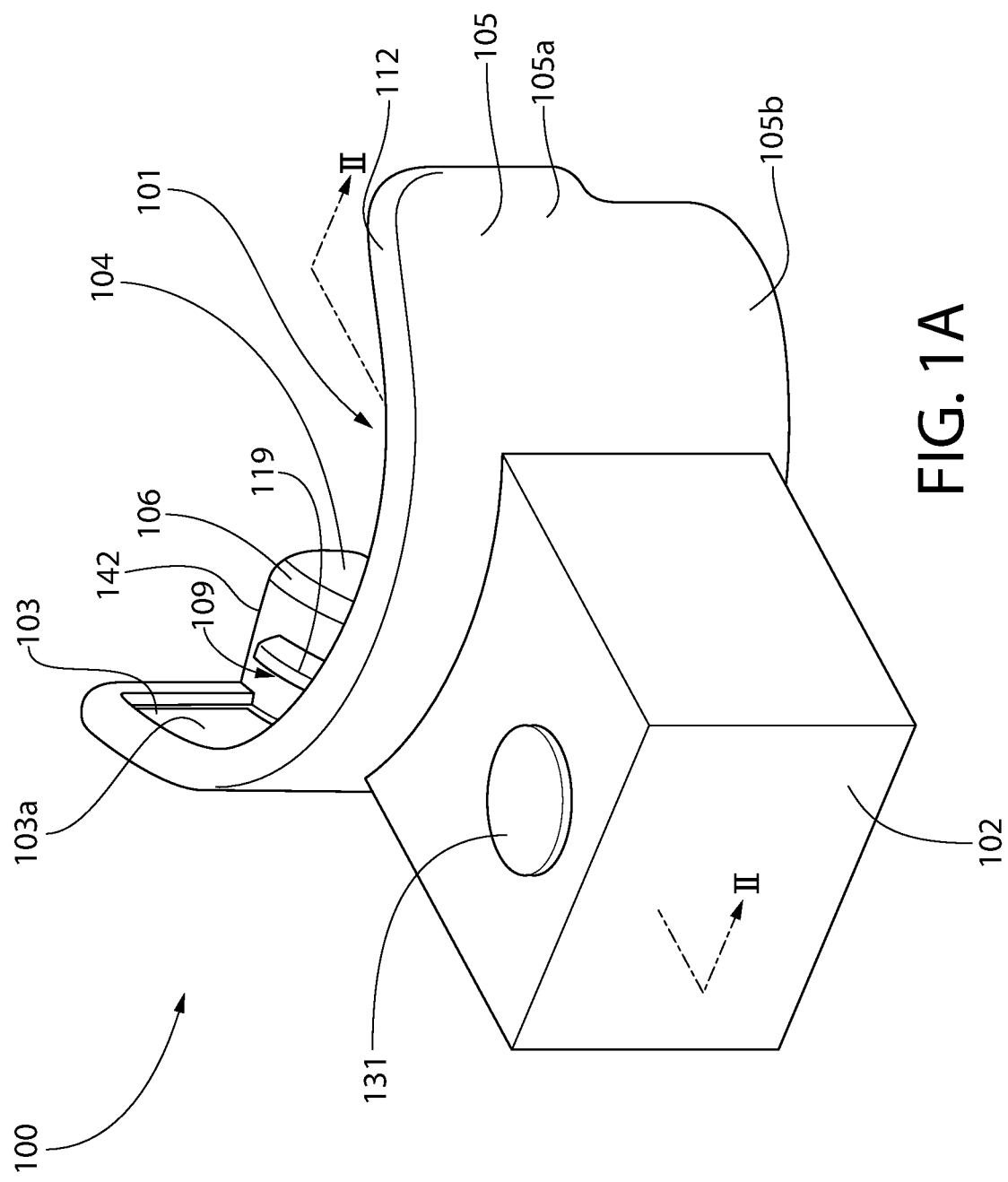
FIG. 1A is a front perspective view of na oral treatment device in accordance with a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Furthermore, it should be noted while the oral treatment device of the present invention is described herein as being a teeth whitening device in some embodiments, it is to be understood that the invention is not so limited. For example, in certain embodiment, the oral treatment device of the present invention can be configured to emit light for other oral treatment purposes, including without limitation, enhancing oral tissue healing, antibacterial purposes, treating tooth sensitivity, disinfecting, cleansing, and combinations thereof. In such other embodiments, the characteristics of the light being emitted by the oral treatment device of the present invention will be selected to achieve the desired treatment, such as wavelength, intensity, power, light density and/or other characteristics. In still other embodiments, the benefit of the oral treatment device can be dictated by the oral care material with which it is used in conjunction therewith. For example, in certain embodiments, the oral care treatment device may be used in conjunction with other oral care materials, including without limitation, antibacterial agents, anti-sensitivity agents, anti-inflammatory agents, anti-attachment agents, plaque indicator agents, flavorants, sensates, breath freshening agents, gum health agents and colorants. Examples of these agents include metal ion agents (e.g., stannous ion agents, copper ion agents, zinc ion agents, silver ion agents) triclosan; triclosan monophosphate, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride (TDEPC), octenidine, delmopinol, octapinol, nisin, essential oils, furanones, bacteriocins, flavans, flavinoids, folic acids, vitamins, minerals, hydrogen peroxide, urea peroxide, sodium percarbonate, PVP-H2O2, polymer-bound perxoxides, potassium nitrates, occluding agents, bioactive glass, arginine salts, arginine bicarbonate, bacalin, polyphenols, ethyl pyruvate, guanidinoethyl disulfide, tartar control agents, anti-stain ingredients, phosphate salts, polyvinylphosphonic acid, PVM/MA copolymers; enzymes, glucose oxidase, papain, ficin, ethyl lauroyl arginate, menthol, carvone, and anethole, various flavoring aldehydes, esters, and alcohols, spearmint oils, peppermint oil, wintergreen oil, sassafras oil, clove oil, sage oil, eucalyptus oil, marjoram oil, cinnamon oil, lemon oil, lime oil, grapefruit oil, and/or orange oil.

Figure 1B:
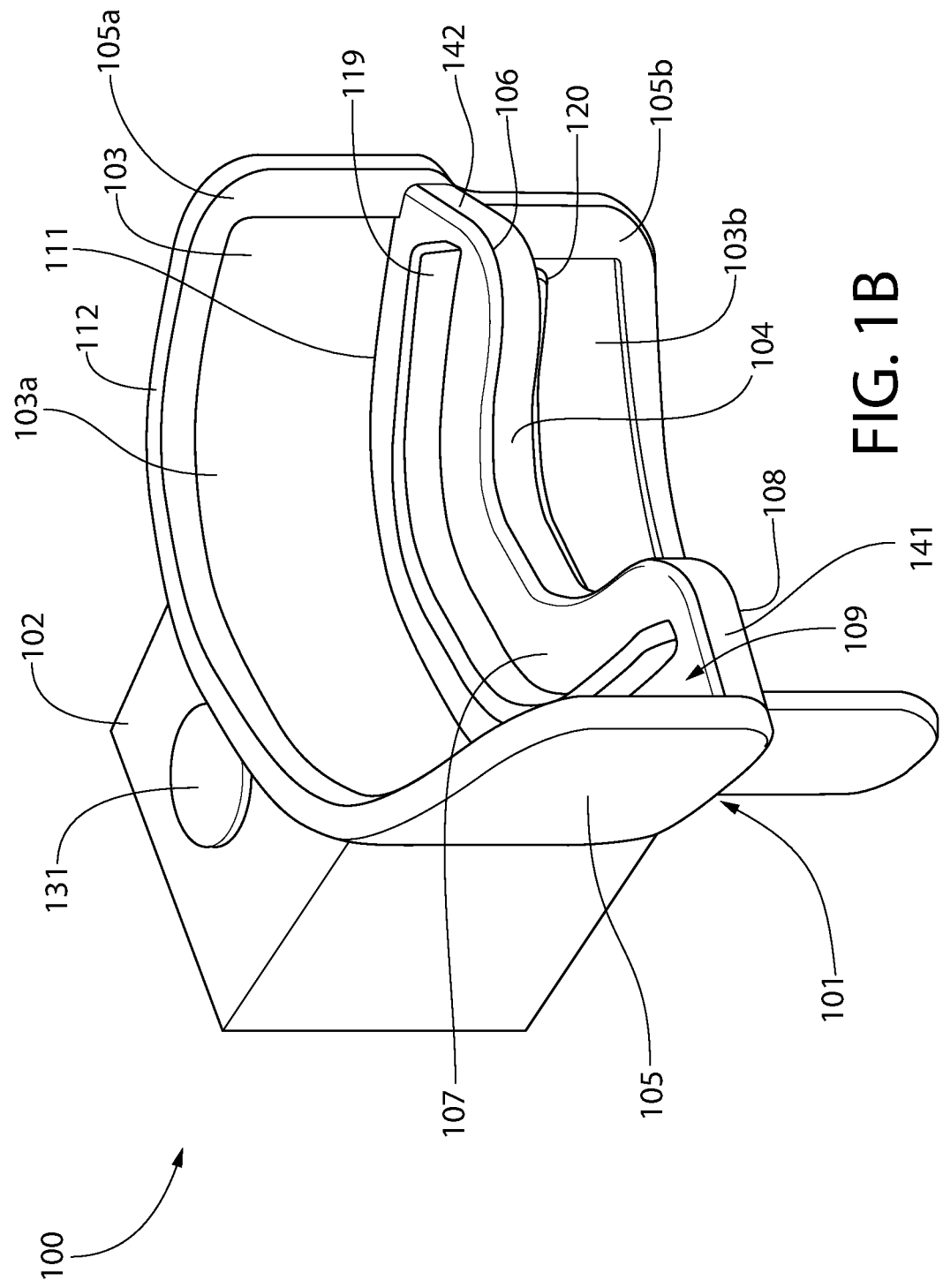
FIG. 1B is a rear perspective view of the teeth device system of FIG. 1A.
Figure 2:
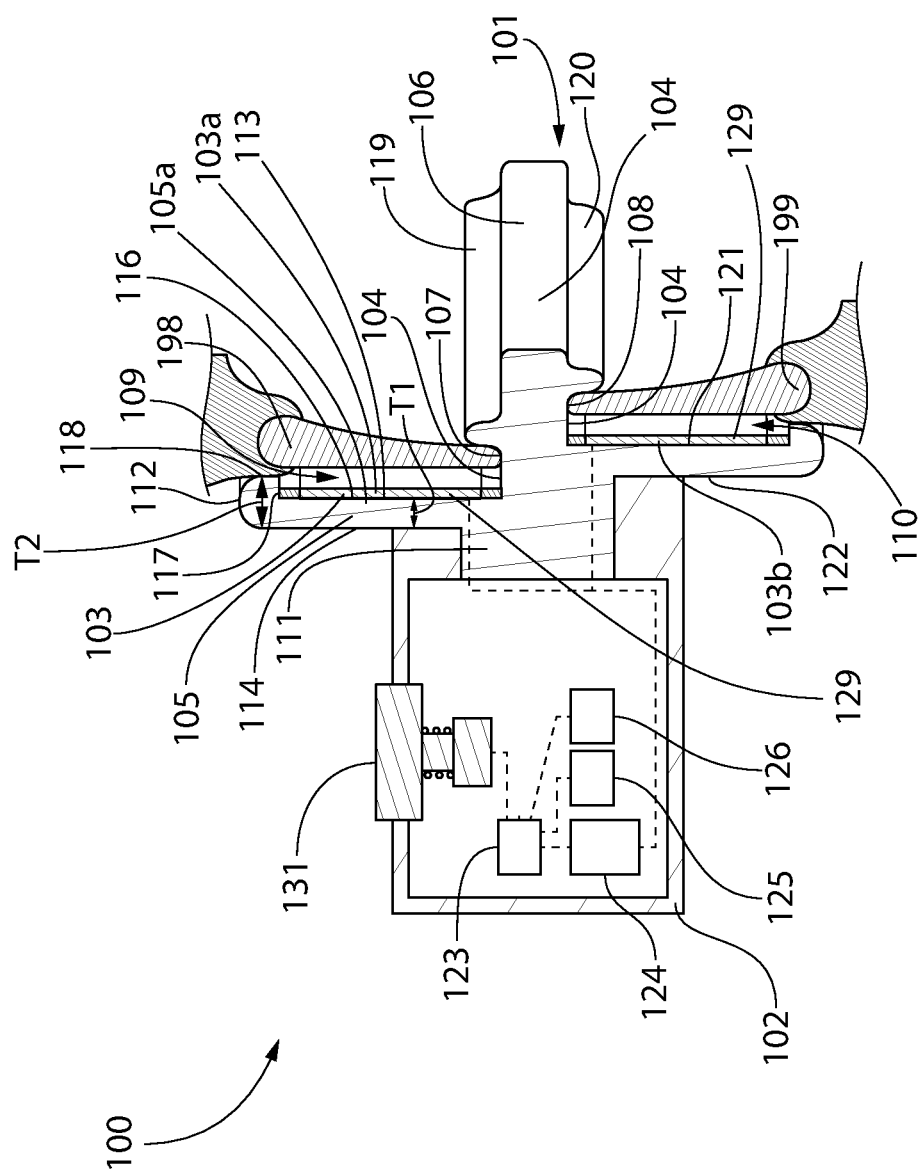
FIG. 2 is a cross-sectional view taken along line II-II of FIG. 1A.

Referring to FIGS. 1A-2 concurrently, an oral treatment device 100 will be described in accordance with an embodiment of the present invention. It is known in oral treatment devices and systems that a more effective whitening result can be achieved by applying a tooth whitening material to a user's teeth and then emitting light or electromagnetic radiation onto the teeth with the tooth whitening material pre-applied thereon in order to activate the tooth whitening material. Many of these systems require that a user manually apply the tooth whitening material to his or her teeth, and then emit the light or electromagnetic radiation onto his or her teeth. The manner in which the light or electromagnetic radiation is applied to the user's teeth has previously been ineffective in that maintaining an equal spacing between the teeth and the electromagnetic radiation source has been difficult to achieve. Furthermore, specific oral treatment devices have been known to be uncomfortable for many users due to the many different shapes of different user's mouths including different tooth positioning and different overall mouth anatomy.

As will be described in greater detail below, the oral treatment device 100 is configured to emit electromagnetic radiation in the form of light that assists with the whitening of teeth. The oral treatment device 100, in some embodiments, can be used by itself to whiten the teeth of the user by simply generating light that is emitted onto the facial surfaces of the user's teeth. In certain other embodiments, however, the oral treatment device 100 may be used in conjunction with a tooth whitening composition. Suitable tooth whitening compositions include, but are not limited to, hydrogen peroxide compositions, carbamide peroxide compositions, calcium peroxide compositions, sodium perborate compositions, combinations thereof, or any other oral care material that is known or discovered to whiten teeth. In such embodiments, the tooth whitening composition can be applied directly to the desired surfaces of the user's teeth (such as the facial surfaces) or can be applied to the oral treatment device 100 itself. Either way, the tooth whitening composition comes into contact with the user's teeth while the light emitted from the oral treatment device 100 is concurrently passed through the tooth whitening composition to irradiate the teeth.

Furthermore, while in the illustrated embodiment the invention is shown such that the light is emitted from the oral treatment device 100 to contact the buccal surfaces of the teeth, in other embodiments the oral treatment system 100 can be configured to emit light onto the lingual, incisal, and/or occlusal surfaces of the teeth instead of and/or in addition to the buccal surfaces. In such embodiments, the lamps can be positioned within the bite plate and/or in the rear walls of the mouthguard that oppose the lingual surfaces of the teeth.

In an exemplified embodiment, the oral treatment device 100 generally comprises a mouthpiece 101, a housing 102 coupled to the mouthpiece 101, and an electromagnetic radiation source 103 coupled to the mouthpiece 101. The electromagnetic radiation source 103 is configured to emit electromagnetic radiation onto the surfaces of the user's teeth as will be described in more detail below.

In certain embodiments, the mouthpiece 101 may be formed of a food grade polymer such as, including without limitation, polyethylene terephthalate (PET), polypropylene (PP), polyethylene naphthalate (PEN), polyethylene (PE), silicone, ethylene propylene diene monomer (EPDM), and other plastics. Of course, the invention is not to be so limited in all embodiments and other materials are possible for construction of the mouthpiece 101. Specifically, in certain embodiments the mouthpiece 101, or portions thereof, may be formed of a compressible or malleable material, which may be one of the materials noted above, or may be a hard rubber, a thermoplastic elastomer, or the like. In some embodiments the mouthpiece 101 may include a hard plastic material that is overmolded with a resilient material. The mouthpiece 101 is intended to be placed within a user's mouth into contact with the user's oral surfaces and saliva, so the material used to form the mouthpiece 101 should be non-toxic and devoid of foul tastes.

The mouthpiece 101 generally comprises a curved wall 105 and a bite platform 106 extending from the curved wall 105. The curved wall 105 and the bite platform 106 collectively form one or more channels for receiving a user's teeth during a tooth whitening session. More specifically, in the exemplified embodiment the curved wall 105 of the mouthpiece 101 comprises an upper curved wall portion 105a extending upward from an upper surface 107 of the bite platform 106 and a lower curved wall portion 105b extending downward from a lower surface 108 of the bite platform 106. The upper curved wall portion 105a and the upper surface 107 of the bite platform 106 collectively form a first channel 109 for receiving a user's upper teeth 198 during a tooth whitening session and the lower curved wall portion 105b and the lower surface 108 of the bite platform 106 collectively form a second channel 110 for receiving a user's lower teeth 199 during a tooth whitening session. During use, the mouthpiece 101 is inserted into a user's mouth such that the bite platform 106 is trapped or sandwiched between the user's upper and lower teeth 198, 199, the upper curved wall portion 105a of the curved wall 105 faces the front surfaces of the user's upper teeth 198, and the lower curved wall portion 105b of the curved wall 105 faces the front surfaces of the user's lower teeth 199. The curved wall 105 may be sandwiched between the inner surfaces of the user's lips and the outer facing surfaces of the user's teeth.

The upper curved wall portion 105a extends from a proximal end 111 that is coupled to the bite platform 106 to a distal end 112. Furthermore, the upper curved wall portion 105a comprises an inner surface 113 that faces the user's teeth when the mouthpiece 101 is in use and an opposing outer surface 114. The inner surface 113 of the upper curved wall portion 105a is concave to correspond with the arch of the user's top teeth. The inner surface 113 of the upper curved wall portion 105a has a recess formed therein. More specifically, a first portion 116 of the inner surface 113 of the upper curved wall portion 105a extends from the bite platform 106 to a shoulder 117 of the upper curved wall portion 105a and a second portion 118 of the inner surface 113 of the upper curved wall portion 105a extends from the shoulder 117 to the distal end 112 of the upper curved wall portion 105a. The first portion 116 of the inner surface 113 of the upper curved wall portion 105a is recessed relative to the second portion 118 of the inner surface 113 of the upper curved wall portion 105a. Stated another way, the upper curved wall portion 105a has a first thickness T1 measured between the outer surface 114 of the upper curved wall portion 105a and the first portion 116 of the inner surface 113 of the upper curved wall portion 105a and a second thickness T2 measured between the outer surface 114 of the upper curved wall portion 105a and the second portion 118 of the inner surface 113 of the upper curved wall portion 105a. The second thickness T2 is greater than the first thickness T1.

The lower curved wall portion 105b has an inner surface 121 and an opposing outer surface 122. The inner surface 121 of the lower curved wall portion 105b is concave to correspond with the arch of the user's bottom teeth. The inner surface 121 of the lower curved wall portion 105b has a recess similar to the recess of the upper curved wall portion 105a described above. Generally, the structure of the lower curved wall portion 105b is the same as the structure of the upper curved wall portion 105a and it will not be repeated herein in the interest of brevity. As can be seen in the embodiment of FIG. 2, the inner surfaces 113, 121 of the upper and lower curved wall portions 105a, 105b of the curved wall 105 are offset from one another. Thus, a longitudinal axis that runs centrally through the upper curved wall portion 105a from the proximal end 111 to the distal end 112 will not intersect the lower curved wall portion 105b. This is done in the exemplified embodiment to enhance the comfort of the mouthpiece 101 during use due to the general shape of a user's bite (with the upper teeth positioned forward of the lower teeth). Of course, the invention is not to be so limited in all embodiments and the inner surfaces 113, 121 of the upper and lower curved wall portions 105a, 105b need not be offset in all embodiments. Despite being offset in the exemplified embodiment, the inner surfaces 113, 121 of the upper and lower curved wall portions 105a, 105b are substantially parallel to one another. The inner surfaces 113, 121 of the upper and lower curved wall portions 105a, 105b may collectively be referred to herein as an inner surface of the curve support plate 105.

The bite platform 106 extends from the curved wall 105 to a distal or terminal end 104. The distal end 104 of the bite platform 106 extends continuously in a non-interrupted manner from a first end 141 of the bite platform 106 to a second end 142 of the bite platform 106. Thus, the distal end 104 of the bite platform 106 is devoid of any notches but rather the distal end 104 of the bite platform 106 forms a smooth and continuous surface or edge of the bite platform 106. Stated another way, there are no openings, slits, or the like that extend to or are formed into the distal end 104 of the bite platform 106. Thus, in certain embodiments the bite platform 106 is a single continuous structure and is not segmented or discontinuous. In some embodiments the upper surface 107, lower surface 108, and distal end 104 of the bite platform 106 are all continuous solid surfaces that are devoid of slits, notches, openings, or the like. The distal end 104 of the bite platform 106 has a curved shape, more specifically a concave shape, and even more specifically a U shape.

The inner surface 113 of the upper curved wall portion 105a is located a first distance from the distal end 104 of the bite platform 106 and the inner surface 121 of the lower curved wall portion 105b is located a second distance from the distal end 104 of the bite platform 106, the first distance being greater than the second distance. Furthermore, the outer surface 122 of the lower curved wall portion 105b is offset from the inner surface 116 of the upper curved wall portion 105a, the inner surface 116 of the upper curved wall portion 105a being positioned a greater distance from the distal end 104 of the bite platform 106 than the outer surface 122 of the lower curved wall portion 105b.

The structure of the upper and lower curved wall portions 105a, 105b of the curved wall 105 facilitate the formation of the first and second channels 109, 110. Specifically, with regard to the upper curved wall portion 105a, when the mouthpiece 101 is properly inserted into a user's mouth, the second portion 118 of the inner surface 113 of the upper curved wall portion 105a contacts the user's gums that are adjacent to the user's upper teeth 198. Because the first portion 116 of the inner surface 113 of the upper curved wall portion 105a is recessed relative to the second portion 118 of the inner surface 113 of the upper curved wall portion 105a, the user's teeth 198 may be spaced apart from the first portion 116 of the inner surface 113 of the upper curved wall portion 105a by the first channel 109. However, the user's teeth 198 are positioned in close proximity to the inner surface 113 of the upper curved wall portion 105a to ensure that the electromagnetic radiation is transmitted onto the teeth 198.

In the exemplified embodiment, the inner surface 113 of the upper curved wall portion 105a has a concave shape that corresponds or is complementary to the collective shape of the front or labial/buccal surfaces of the user's top teeth 198 and the inner surface 121 of the lower curved wall portion 105b has a concave shape that corresponds or is complementary to the collective shape of the front or labial/buccal surfaces of the user's bottom teeth 199. More specifically, the inner surface 113 of the upper curved wall portion 105a has a shape that corresponds to at least a portion of the maxillary arch of the user's teeth and the inner surface 121 of the lower curved wall portion 105b has a shape that corresponds to at least a portion of the mandibular arch of the user's teeth. Similarly, the first channel 109 has an arcuate or curved shape that corresponds to the shape of the maxillary arch of the user's teeth and the second channel 110 has an arcuate or curved shape that corresponds to the shape of the mandibular arch of the user's teeth. This enhances the conformance of the mouthpiece 101 to a user's mouth during use. Of course, each user may have a different shaped maxillary arch, mandibular arch, and/or general mouth shape. Thus, the oral treatment device 100 in accordance with the present invention may include additional features to enhance flexibility of the mouthpiece 101, described in detail below with reference to FIGS. 3A-5D.

The bite platform 106 extends from the curved wall 105 at a location between the upper and lower curved wall portions 105a, 105b of the curved wall 105. In the exemplified embodiment the bite platform 106 and the curved wall 105 connect at an approximately 90° angle, although the invention is not to be so limited in all embodiments and other angles of connection between the bite platform 106 and the curved wall 105 are possible in other embodiments. The bite platform 106 forms a horizontal biting surface for the user to engage with his or her teeth 198, 199 to retain the mouthpiece 101 in a desired position within the user's mouth during a treatment session.

The bite platform 106 comprises a first ridge 119 extending upwardly from the upper surface 107 of the bite platform 106 and a second ridge 120 extending downwardly from the lower surface 108 of the bite platform 106. In the exemplified embodiment, each of the first and second ridges 119, 120 are elongated and arcuate shaped protrusions that extend from the bite platform 106 in opposite directions. Furthermore, in the exemplified embodiment the first ridge 119 is a curved ridge having a curvature that matches the collective curvature of the rear surfaces (i.e., lingual surfaces) of the user's upper teeth and the second ridge 120 is a curved ridge having a curvature that matches the collective curvature of the rear surfaces (i.e., lingual surfaces) of the user's lower teeth. Of course, the invention is not to be so limited in all embodiments and the first and second ridges 119, 120 need not be elongated or arcuate in all embodiments. Specifically, in some embodiments the first and second ridges 119, 120 may be formed by a plurality of discrete protuberances rather than being a single continuous ridge.

The first ridge 119 is spaced apart from the upper curved wall portion 105a by a gap (i.e., by at least a portion of the first channel 109) and the second ridge 120 is spaced apart from the lower curved wall portion 105b by a gap (i.e., by at least a portion of the second channel 110). In the exemplified embodiment, the gap between the first ridge 119 and the upper curved wall portion 105a and the gap between the second ridge 120 and the lower curved wall portion 105b have the same width so that when the mouthpiece 101 is inserted into a user's mouth, the spacing between the user's upper teeth and the upper curved wall portion 105a is identical to the spacing between the user's lower teeth and the lower curved wall portion 105b.

The first ridge 119 provides a structure for the rear surfaces of the user's upper teeth 198 to rest against during use of the mouthpiece 101 and the second ridge 120 provides a structure for the rear surfaces of the user's lower teeth 199 to rest against during use of the mouthpiece 101. Thus, when the user inserts the mouthpiece 101 into his or her mouth, the user will know exactly where to position the teeth on the mouthpiece 101 based on the location of the first and second ridges 119, 120 in order to ensure that adequate spacing between the teeth and the curved wall 105 is provided. As can be seen in FIG. 2, in the exemplified embodiment the first and second ridges 119, 120 are offset from one another. This is done in the exemplified embodiment to enhance user comfort because the offset nature of the first and second ridges 119, 120 imitates the offset nature of the user's upper and lower teeth (typically a user's upper teeth extend further forward towards the front of the mouth than the user's lower teeth). Of course, in still other embodiments the first and second ridges 119, 120 may be altogether omitted and proper spacing between the user's teeth and the curved wall 105 can be achieved by the recessed structure of the portions of the curved wall 105 as described herein above.

Although the invention is illustrated and described herein such that it includes the upper and lower curved wall sections 105a, 105b, the invention is not to be so limited in all embodiments. In certain other embodiments, the mouthpiece 101 may include the bite platform 106 and only one of the upper and lower curved wall sections 105a, 105b. In this manner, one mouthpiece that includes the bite platform 106 and the upper curved wall section 105a can be used for treating the user's upper teeth. A separate mouthpiece that includes the bite platform 106 and the lower curved wall section 105b can be used for treating the user's lower teeth. Thus, an alternative embodiment includes two separate mouthpieces, one for treatment of the upper teeth and one for treatment of the lower teeth. This alternative embodiment may be advantageous when it is desired to only treat the upper teeth or the lower teeth, but can also be used to treat both the upper and lower teeth simultaneously. Thus, the mouthpiece 101 can be a single integral structure for treating the upper and lower teeth simultaneously or two separate structures, one for treating the upper teeth and another for treating the lower teeth. Alternatively, a single mouthpiece having only the bite platform 106 and one curved wall section may be used for treating both the upper and lower teeth in a consecutive or sequential manner as desired.

Still referring to FIGS. 1A-2, as noted above the oral treatment device 100 further comprises the electromagnetic radiation source 103 coupled to the mouthpiece. In the exemplified embodiment, the electromagnetic radiation source 103 comprises a first electromagnetic radiation source 103a coupled to the upper curved wall portion 105a and a second electromagnetic radiation source 103b coupled to the lower curved wall portion 105b. More specifically, in the exemplified embodiment the first electromagnetic radiation source 103a is coupled to the first portion 116 of the inner surface 113 of the upper curved wall portion 105a such that the first electromagnetic radiation source 103a is located within the recess of the upper curved wall portion 105a. Similarly, in the exemplified embodiment the second electromagnetic radiation source 103b is coupled to the inner surface 121 of the lower curved wall portion 105b such that the second electromagnetic radiation source 103b is located within the recess of the lower curved wall portion 105b. Of course, the invention is not to be so limited in all embodiments and the first electromagnetic radiation source 103a may be coupled to the upper surface 107 of the bite platform 106 in some embodiments and/or the second electromagnetic radiation source 103b may be coupled to the lower surface 108 of the bite platform 106 in some embodiments. In other embodiments, the first electromagnetic radiation source 103a may be coupled to the upper surface 107 of the bite platform 106 and the upper curved wall portion 105a and the second electromagnetic radiation source 103b may be coupled to the lower surface 108 of the bite platform 106 and the lower curved wall portion 105b.

Although the first electromagnetic radiation source 103a is positioned within the recess of the upper curved wall portion 105a, in the exemplified embodiment the exposed outer surface of the first electromagnetic radiation source 103a remains recessed relative to the second portion 118 of the inner surface 113 of the upper curved wall portion 105a. This ensures that a space remains between the user's teeth 198 and the first electromagnetic radiation source 103a so that tooth whitening material can be located within the space during the whitening regimen. The same is true of the second electromagnetic radiation source 103b in that it is recessed relative to the second portion of the inner surface 121 of the lower curved wall portion 105b.

Although the electromagnetic radiation sources 103a, 103b are described and illustrated herein as being coupled to the inner surface 113 of the curved wall 105, the invention is not to be so limited. In some embodiments the electromagnetic radiation source may be positioned at other locations within or adjacent to the oral treatment device 100. Thus, the electromagnetic radiation source 103 may be configured to emit electromagnetic radiation from the curved wall 105 regardless of the positioning or specific location of the electromagnetic radiation source 103. Specifically, the electromagnetic radiation source 103 may be coupled to a housing attached to the mouthpiece 101 and electromagnetic radiation emitted from the electromagnetic radiation source 103 may be emitted through the curved wall 105 by transmittance through one or more light pipes. In some embodiments any desired positioning of the electromagnetic radiation source 103 may be possible so long as the electromagnetic radiation is emitted from the curved wall 105 for application or transmittance onto a user's teeth as described herein.

The electromagnetic radiation source 103 is coupled to the mouthpiece 101 in such a manner that it can emit electromagnetic radiation onto the surfaces of the user's teeth 198, 199 when the user's teeth 198, 199 are positioned within the first and second channels 109, 110. Specifically, when the mouthpiece 101 is properly positioned within a user's mouth, the user's upper teeth 198 are located within the first channel 109 and the user's lower teeth 199 are located within the second channel 110. In this position, the electromagnetic radiation source 103 can properly emit electromagnetic radiation onto surfaces of the user's teeth 198, 199. In the exemplified embodiment, the first and second electromagnetic radiation sources 103a, 103b are coupled to the inner surfaces 113, 121 of the upper and lower curved wall portions 105a, 105b, respectively. Thus, the first and second electromagnetic radiation sources 103a, 103b are curved so as to have concave surfaces that face the user's teeth when the mouthpiece 101 is positioned within the user's mouth. During use, the first and second electromagnetic radiation sources 103a, 103b are configured to emit the electromagnetic radiation onto the front surfaces (i.e., the labial/buccal surfaces) of the user's upper and lower teeth 198, 199, respectively. In certain embodiments, the first and second electromagnetic radiation sources 103a, 103b are configured to emit the electromagnetic radiation orthogonally into contact with surfaces of the user's upper and lower teeth 198, 199 (i.e., at an approximately 90° angle). Of course, electromagnetic radiation can be emitted onto other surfaces or portions of the user's upper and lower teeth 198, 199 depending on the portion of the mouthpiece 101 to which the first and second electromagnetic radiation sources 103a, 103b are coupled as described herein above.

In certain embodiments, the first and second electromagnetic radiation sources 103a, 103b may be enclosed within the mouthpiece 101 such that a portion of the mouthpiece 101 covers the first and second electromagnetic radiation sources 103a, 103b. Thus, the electromagnetic radiation sources 103a, 103b may not be exposed, but rather may be covered by the portions of the mouthpiece 101 which may protect the electromagnetic radiation sources 103a, 103b against damage from saliva and the teeth. In such embodiments, the portion of the mouthpiece 101 that covers the first and second electromagnetic radiation sources 103a, 103b may be transparent or translucent to permit the electromagnetic radiation emitted by the first and second electromagnetic radiation sources 103a, 103b to pass therethrough.

The electromagnetic radiation source 103 (and more specifically, each of the first and second electromagnetic radiation sources 103a, 103b) can be any type of electromagnetic radiation source 103 desired that emits electromagnetic radiation when power is supplied thereto. In certain embodiments, the electromagnetic radiation source 103 comprises a flexible circuit 129 with a plurality of first illumination elements (not illustrated) thereon. One of the flexible circuits 129 may be coupled to each of the upper and lower curved wall portions 105a, 105b. In certain embodiments the plurality of first illumination elements may be light emitting diodes (LEDs), and the terms illumination elements and LEDs may be used interchangeably herein. Although described herein as being LEDs, the first illumination elements may in certain embodiments be any type of light source, particularly solid state light sources, which may include LEDs, OLEDs, HBLEDs, electroluminescent elements, or the like.

The flexible circuit 129 may be a flat, flexible substrate or sheet that appears to glow when power is provided thereto. The flexible circuit 129 may have flat, planar opposing major surfaces (i.e., front and rear surfaces) in its original form but the flexible circuit 129 may flex to fit the contours of the concave inner surfaces 113, 121 of the curved wall 105 during manufacturing.

In certain embodiments the flexible circuit 129 of the electromagnetic radiation source 103 may be a printed light emitting diode. Printed LEDs may be formed by depositing micro LED chips via a conductive ink formulation that can be printed in any shape to best conform to the teeth and jaw structure, which is ideal for optimized efficacy. Specifically, gallium nitride may be used to form the LEDs in some embodiments, which may then be mixed with resin and binders to form an ink, and a standard screen printer may be used to deposit the resulting ink over a desired surface. The substrate or flexible circuit 129 can be a thin plastic film or paper and can be formed to match the contours of the mouthpiece 101. In certain embodiments, it is merely desirable that the electromagnetic radiation source 103 be electrically conductive, flexible, and able to conform closely to the contours of the teeth. In that regard, the electromagnetic radiation source 103 can be printed inorganic LEDs, micro conventional LEDs that are surface mounted to a flexible substrate/circuit, organic LEDs (OLEDs), or electroluminescence. In still other embodiments, the electromagnetic radiation source 103 can be any of the LEDs noted herein mounted to a rigid rather than a flexible substrate.

In certain embodiments, the electromagnetic radiation source 103 is configured to emit electromagnetic radiation in the range of 385 nm to 520 nm, although the invention is not to be so limited and electromagnetic radiation outside of the above-noted range is also possible. Many of the first illumination elements may be positioned on or embedded within the flexible circuit 129. In some embodiments there may be thousands or even millions of the first illumination elements positioned on or embedded within the flexible circuit 129. Because of the large number of first illumination elements formed on or embedded within the flexible circuit 129, even if some of the first illumination elements burn out or are non-operable, the electromagnetic radiation source 103 will still be capable of operating effectively for tooth whitening. The invention is not to be limited by the number of the first illumination elements in all embodiments, but it is desirable in certain embodiments that the number of the first illumination elements is sufficient to ensure electromagnetic radiation is emitted onto each tooth in the manner described herein.

In the exemplified embodiment, the oral treatment device 100 further comprises the housing 102 coupled to the mouthpiece 101. In the exemplified embodiment the housing 102 extends from the curved wall 105 of the mouthpiece 101 in a first direction and the bite platform 106 extends from the curved wall 105 of the mouthpiece in a second direction that is opposite to the first direction. Thus, the bite platform 106 extends from the inner surfaces 113, 121 of the curved wall 105 and the housing 102 extends from the outer surfaces 114, 122 of the curved wall 105 (it should be appreciated that the shoulder 117 described above also extends from the inner surfaces 113, 121 of the curved wall 105 in the same direction as the bite platform 106). In the exemplified embodiment, the housing 102 is depicted generically as a box. However, the invention is not to be so limited and the shape of the housing 102 can be modified into any desired shape for aesthetic or functional reasons.

In the exemplified embodiment, within the housing 102 is positioned a processor 123, a power supply 124, a timer 125, and a heater 126 that are operably coupled together. More specifically, the processor 123 is operably coupled to each of the power source 124, the timer 125, and the heater 126. The processor 123 may be any suitable microprocessor based programmable logic controller, personal computer, or the like that has memory for storing various instructions to control the operation of the electromagnetic radiation source 103. The processor 123 is programmed with algorithms to receive data from the various other electrical components and sensors, analyze the data, and cause the electrical components to operate in a desired or predetermined manner based on instructions that are stored in the memory of the processor 123.

In the exemplified embodiment, the power source 124 is operably coupled to the processor 123 and to the electromagnetic radiation source 103 (and more specifically to each of the first and second electromagnetic radiation sources 103a, 103b). The electrical connections between the various electrical components, and particularly between the power source 124 and the electromagnetic radiation source 103, is illustrated in the figures in dotted lines. The power source 124 may be one or more batteries, battery cells, printed batteries, rechargeable batteries, super capacitors, or a control circuit that store electrical energy that can be used to power the electromagnetic radiation source 103 as desired. Alternatively, the power source 124 may be omitted and instead the electronic components of the device may be powered by a plug that is coupled to a power supply, such as a curved wall socket.

In the exemplified embodiment, the oral treatment device 100 also comprises an actuator 131. In the exemplified embodiment, the actuator 131 is a depressible button. However, the invention is not to be so limited and the actuator 131 can be any type of device that upon actuation powers on and/or off one or more of the electrical components stored within the housing 102. For example, the actuator 131 can be a slide switch, a touch pad, or any other component that upon actuation causes the oral treatment device 100 to function by emitting electromagnetic radiation onto a user's teeth. The actuator 131 is operably coupled to the processor 123 so that upon depressing or otherwise actuating the actuator 131, the processor 123 initiates operation of the oral treatment device 100, and specifically powers on the electromagnetic radiation source 103. The actuator 131 may be an on/off button or the like and may initiate the operation of the oral treatment device 100 for a pre-determined period of time as calculated by the timer 125. The actuator 131 may also initiate the application of heat onto a user's teeth via the heater 126. In certain embodiments, more than one actuator may be used so that different actuators initiate operation of different components (i.e., the electromagnetic radiation source 103, the heater 126, etc.).

As noted above, different people have different mouth shapes and different tooth arch shapes. As a result, it is preferable that a device intended to be placed within a user's mouth have some flexibility in its shape. This can ensure that an appropriate spacing between the electromagnetic radiation source 103 and the user's teeth is always achieved regardless of the user's mouth and teeth arch shape in order to effectively and efficiently apply the electromagnetic radiation onto the user's teeth. Thus, in certain embodiments the oral treatment device 100 may improve teeth whitening performance by providing means for the mouthpiece 101 to conform to the user's teeth and mouth anatomy. It may be desirable to maintain a consistent and minimal gap between the electromagnetic radiation source 103 and the user's teeth. Thus, the mouthpiece 101 or the oral treatment device 100 may include features that enhance the flexibility of the mouthpiece 101.

Referring to FIGS. 3A-3D concurrently, one embodiment of a oral treatment device 200 having increased flexibility will be described. The oral treatment device 200 is identical to the oral treatment device 100 described above except with regard to the features described specifically with regard to the oral treatment device 200. A similar numbering scheme will be used for the oral treatment device 200 as was used for the oral treatment device 100 except that the 200-series of numbers will be used. If a feature of the oral treatment device 200 is numbered but not described, the description of the similar feature with regard to the oral treatment device 100 applies. If a feature of the oral treatment device 200 is not numbered or described, the description of the similar feature of the oral treatment device 100 may apply.

The oral treatment device 200 generally comprises a mouthpiece 201 comprising a curved wall 205 and a bite platform 206. The curved wall 205 comprises a concave inner surface 213. The bite platform 206 extends from the concave inner surface 213 of the curved wall 205 and terminates in a distal end 204. In the exemplified embodiment the bite platform 206 extends substantially perpendicularly from the concave inner surface 213 of the curved wall 205, although the oral treatment device 200 is not to be so limited in all embodiments. The bite platform 204 comprises an upper surface 207 and a lower surface 208. Furthermore, similar to the discussion above, an electromagnetic radiation source 203 is coupled to the concave inner surface 213 of the curved wall 205. The electromagnetic radiation source 203 is operably coupled to a power source as described above in order to power the electromagnetic radiation source 203 to emit electromagnetic radiation (such as light) onto a user's teeth that are positioned adjacent to the electromagnetic radiation source 203 during use of the oral treatment device 200.

In order to permit the mouthpiece 201 to have an increased amount of flexibility, in the exemplified embodiment the bite platform 206 comprises at least one collapsible region 250. The collapsible region 250 of the bite platform 206 permits the mouthpiece 201 to be alterable between a biased state (FIG. 3A) in which the curved wall 205 has a first curvature and a flexed state (FIG. 3B) in which the curved wall 205 has a second curvature that is different than the first curvature. Specifically, pressure on opposing ends of the mouthpiece 201 (see arrows F in FIGS. 3B and 4B) causes the mouthpiece 201 to alter from the biased state to the flexed state. The mouthpiece 201 alters back into the biased state upon cessation of the force. Thus, the biased state is the normal state of the mouthpiece 201 when no forces are acting thereon. In certain embodiments the mouthpiece 201 may be alterable so that the curvature increases or decreases in the flexed state relative to the curvature in the biased (or non-flexed or normal) state. The force can be applied by a user's hand squeezing the opposing ends of the mouthpiece 201 or by the orbicularis oris muscle of the mouth (or some other muscle within a user's mouth) that exerts pressure to mold or shape the mouthpiece 201 to conform to the user's mouth.

As used herein, the term curvature refers to the degree to which something is curved. In the exemplified embodiment, the first curvature of the mouthpiece 201 in the biased state is less than the second curvature of the mouthpiece 201 in the flexed state. Thus, by applying a force F onto opposing ends of the mouthpiece 201 (the forces F being applied in a direction towards one another), the curvature of the curved wall 205 of the mouthpiece 201 increases. As a result, a distance D1 between the opposing ends of the curved wall 205 in the biased state i.e., at the first curvature) is greater than a distance D2 between the opposing ends of the curved wall 205 in the flexed state (i.e., at the second curvature). As the opposing ends of the curved wall 205 are brought closer together in response to the forces the curvature of the curved wall 205 increases.

The bite platform 206 has a width W1 measured from the concave inner surface 213 of the curved wall 205 to the distal end 204 of the bite platform 206. In the exemplified embodiment, the width W1 of the bite platform 206 is constant from the first end 241 of the bite platform 206 to the second end 242 of the bite platform 206. Thus, there are no cutouts, notches, slits, openings, holes, or the like formed into the bite platform 206, but it is a continuously extending structure. The width W1 of the bite platform 206 is the same in the biased state and in the flexed state as flexure of the mouthpiece 201 does not affect the width W1 of the bite platform 206 in this embodiment along any portion of its length.

In the exemplified embodiment, the collapsible region 250 of the bite platform 206 is a portion of the bite platform 206 that has a wavy or undulating appearance. Specifically, the upper and lower surfaces 207, 208 of the bite platform 206 undulate in the collapsible region 250. More specifically, within the collapsible region 250, the upper and lower surfaces 207, 208 of the bite platform 206 have peaks and valleys as the collapsible region 250 has an accordion-like shape. The collapsible region 250 of the bite platform 206 may have a W-like shape in profile, an M-like shape in profile, or the shape of multiple Vs (or upside-down Vs) connected together. The collapsible region 250 of the bite platform 206 extends from the concave inner surface 213 of the curved wall 305 to the distal end 304 of the bite platform 206 along a portion of the axial length of the bite platform 206. Thus, in the exemplified embodiment the collapsible region 250 of the bite platform 206 extends the entire width W1 of the bite platform 206 along a portion of the axial length of the bite platform 206, the axial length of the bite platform 206 measured between the first and second ends 241, 242 of the bite platform 206.

Furthermore, in the exemplified embodiment of FIGS. 3A-3D, the bite platform 206 comprises a first non-collapsible region 260 and a second non-collapsible region 270, the collapsible region 250 being located between the first and second non-collapsible regions 260, 270. While the upper and lower surfaces 207, 208 of the bite platform 206 are wavy or undulating in the collapsible region 250, the upper and lower surfaces 207, 208 of the bite platform 206 are substantially flat or planar in the first and second non-collapsible regions 260, 270. In this embodiment, the first non-collapsible region 260 of the bite platform 206 extends uninterrupted from the first end 241 of the bite platform 206 to a first end 243 of the collapsible region 250 of the bite platform 206. The second non-collapsible region 270 of the bite platform 206 extends uninterrupted from the second end 242 of the bite platform 206 to a second end 244 of the collapsible region 250 of the bite platform 206. Thus, the collapsible region 250 of the bite platform 206 may be located centrally between the first and second non-collapsible regions 260, 270 of the bite platform 206 along an axis A-A of the bite platform 206. Of course, the invention is not to be so limited in all embodiments and in other embodiments the location of the collapsible region 250 may be modified as desired.

The first and second non-collapsible regions 260, 270 of the bite platform 206 have a first thickness TB1 measured from the lower surface 208 of the bite platform 206 to the upper surface 207 of the bite platform 206. The collapsible region 250 of the bite platform 206 has a second thickness TB2 measured from the lower surface 208 of the bite platform 206 to the upper surface 207 of the bite platform 206. The second thickness TB2 is less than the first thickness TB1. The reduced thickness and wavy configuration of the collapsible region 250 of the bite platform 206 permits the collapsible region 250 to collapse or spring/flex inwardly in response to forces being applied to the mouthpiece 201 as described herein and to return to its original shape upon the cessation of forces applied to the mouthpiece 201.

Similar to the oral treatment device 100, the oral treatment device 200 comprises a ridge 219 extending upward from the upper surface 207 of the bite platform 206 and a ridge 220 extending downward from the lower surface 208 of the bite platform 206. More specifically, the ridge 219 extends in a discontinuous manner such that the ridge 219 comprises a first portion 219a located on the first non-collapsible region 260 of the bite platform 206 and a second portion 219b located on the second non-collapsible region 270 of the bite platform 206. The ridge 219 does not extend from the bite platform 206 within the collapsible region 250. Thus, the first and second portions 219a, 219b of the ridge 219 are spaced apart from one another by the collapsible region 250 of the bite platform 206 so that the ridge 219 does not interfere with the flexing of the collapsible region 250 of the bite platform 206.

Figure 3A:
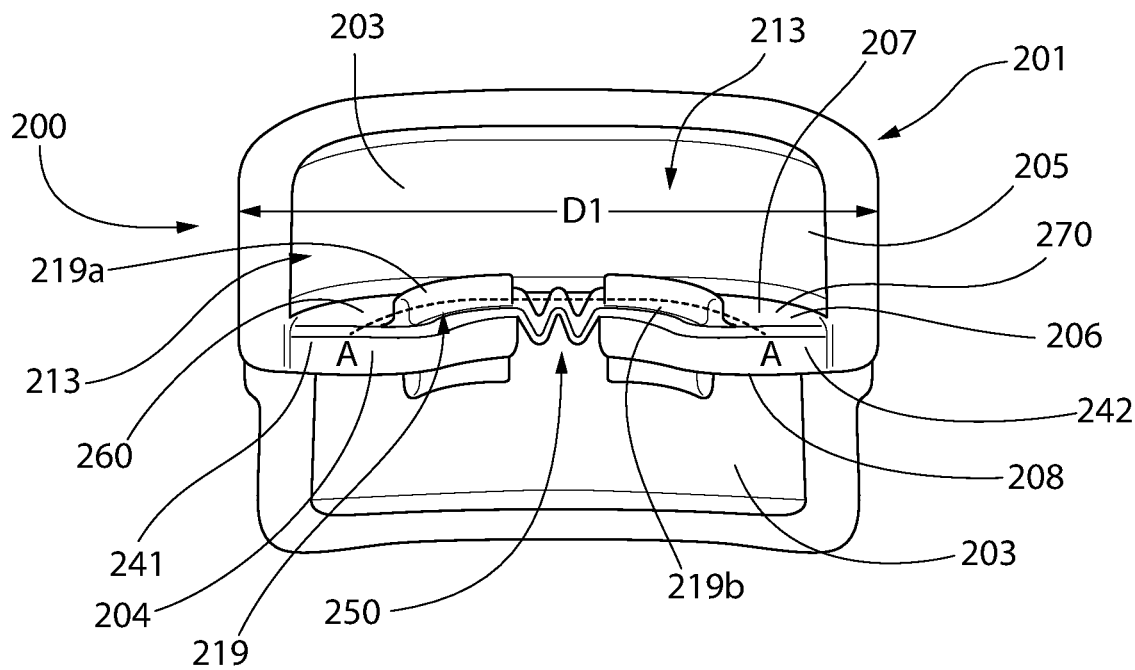
FIG. 3A is a front view of an oral treatment device including a mouthpiece and an electromagnetic radiation source in accordance with a second embodiment of the present invention, wherein the mouthpiece is in a biased state.
Figure 3B:
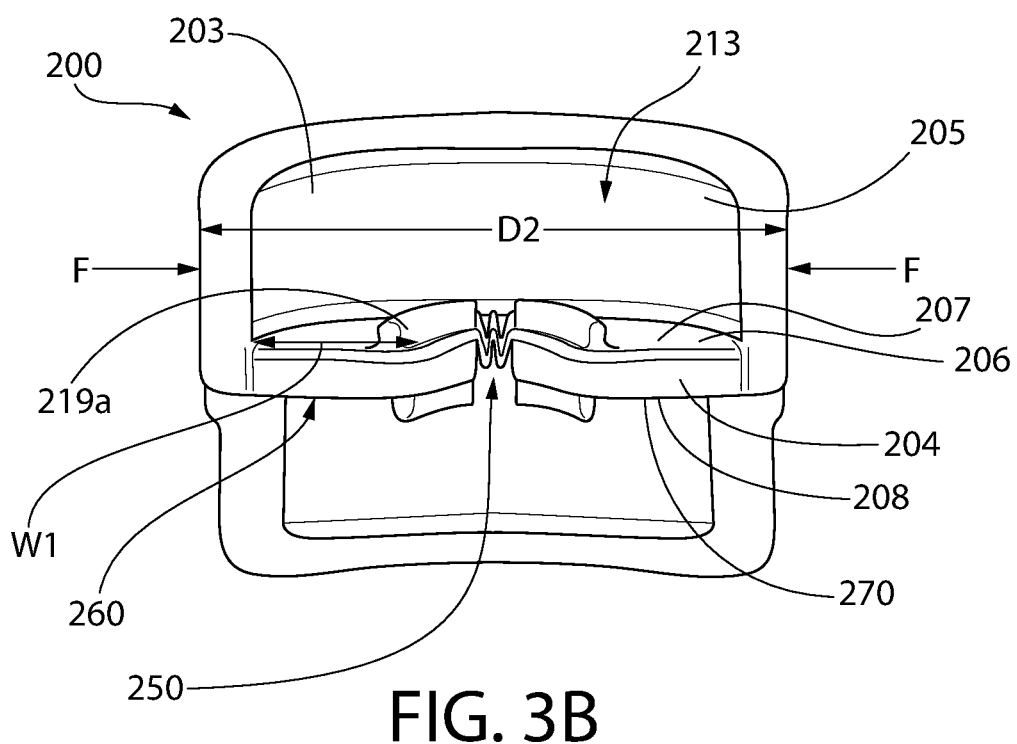
FIG. 3B is a front view of the oral treatment device of FIG. 3A wherein the mouthpiece is in a flexed state.
Figure 3C:
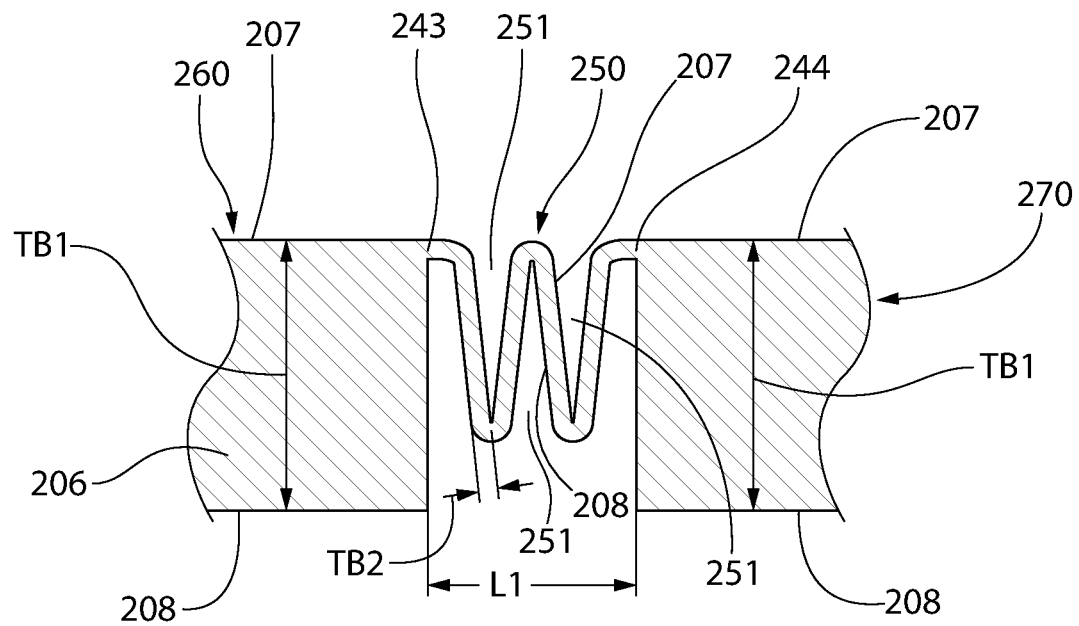
FIG. 3C is a schematic illustration of a collapsible region of the mouthpiece of FIG. 3A when the mouthpiece is in the biased state.
Figure 3D:
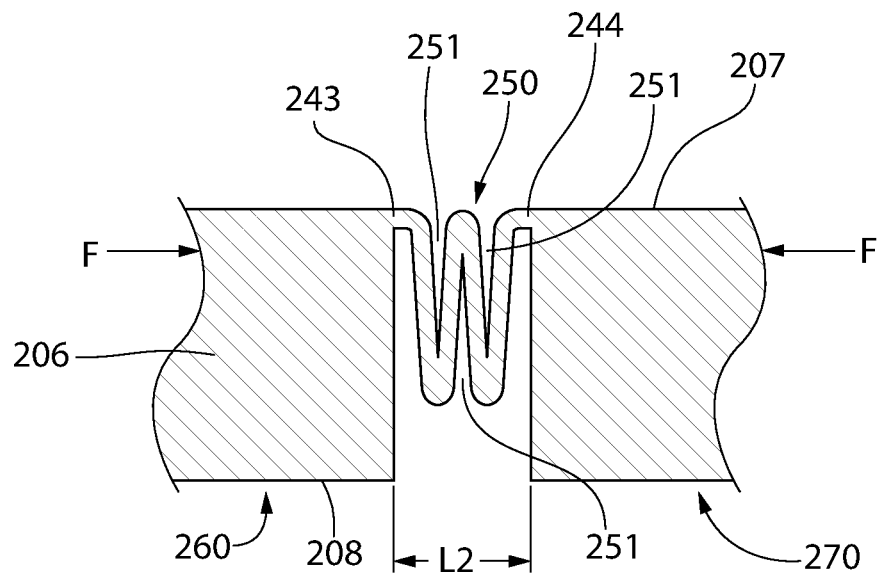
FIG. 3D is a schematic illustration of the collapsible region of the mouthpiece of FIG. 3B when the mouthpiece is in the flexed state.
Figure 4A:
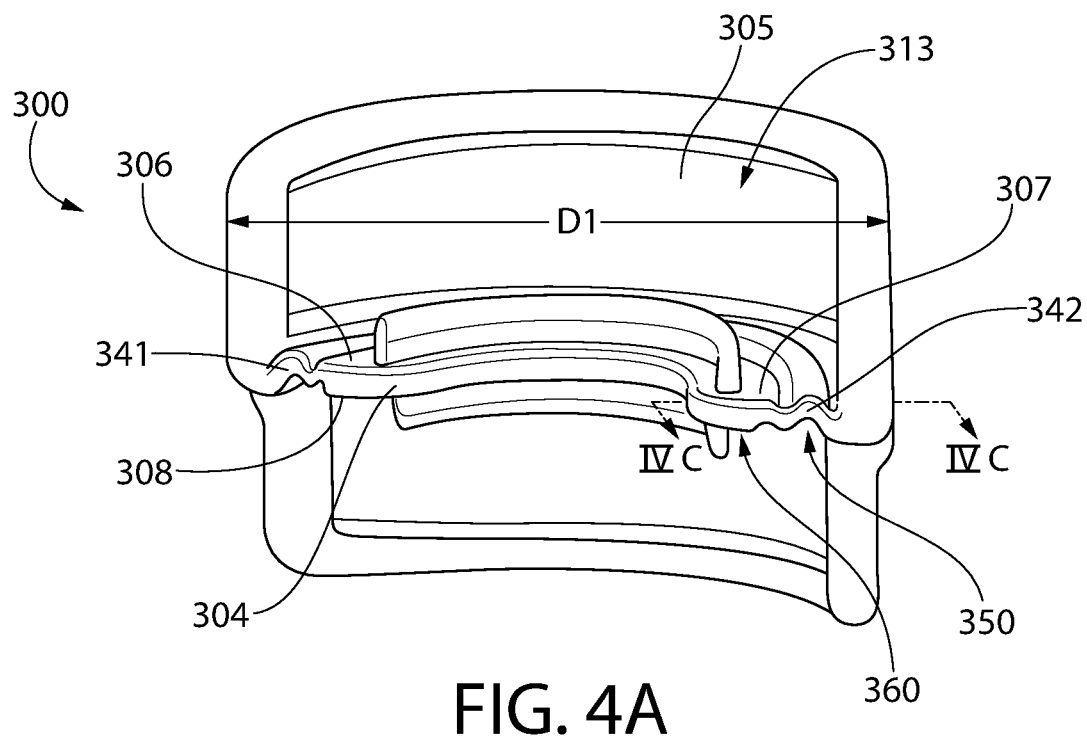
FIG. 4A is a front view of an oral treatment device including a mouthpiece and an electromagnetic radiation source in accordance with a third embodiment of the present invention, wherein the mouthpiece is in a biased state.
Figure 4B:
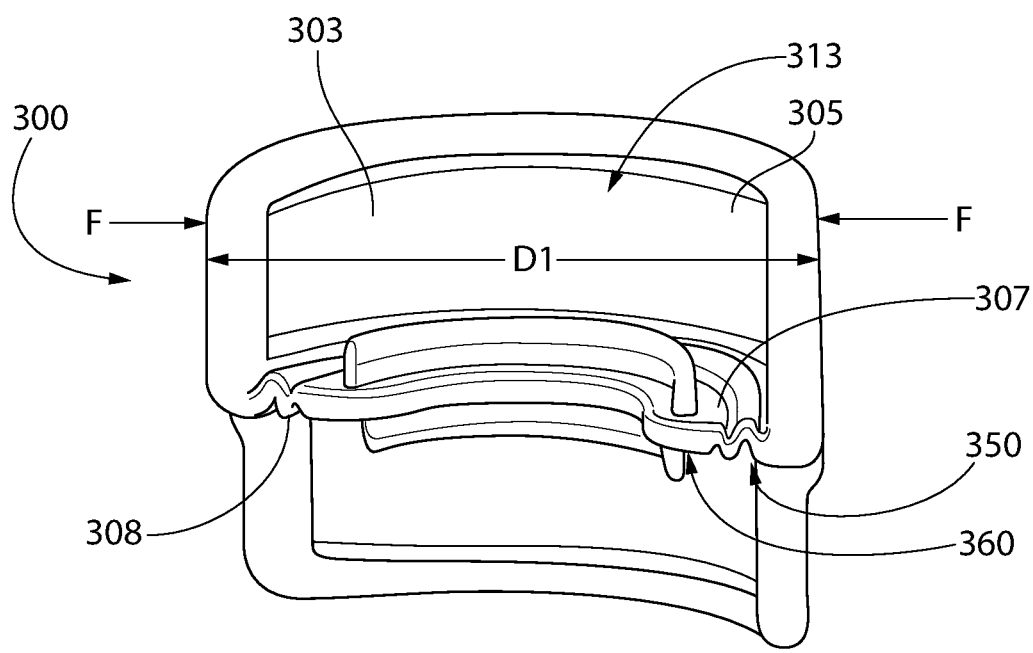
FIG. 4B is a front view of the oral treatment device of FIG. 4A wherein the mouthpiece is in a flexed state.
Figure 4C:
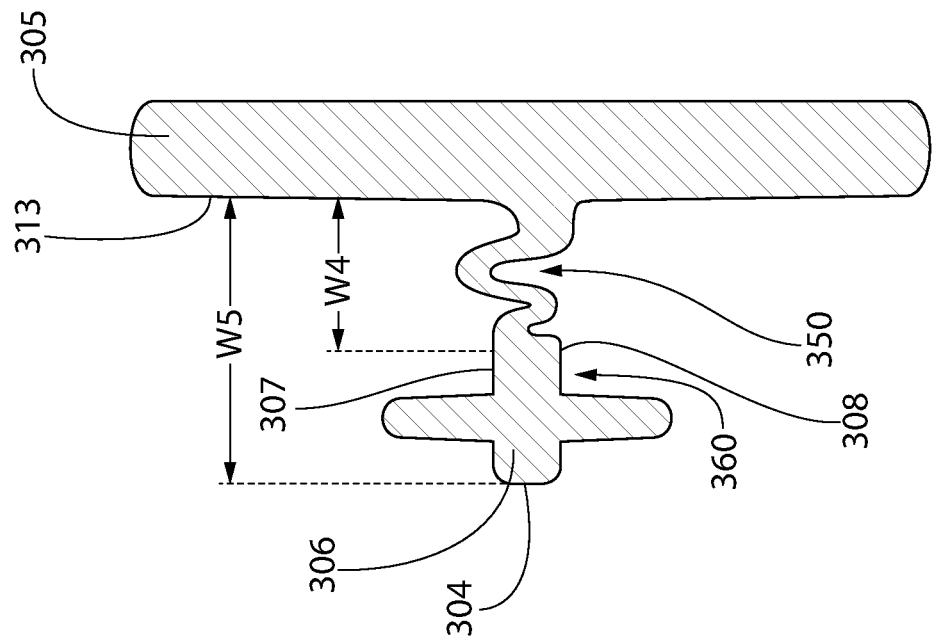
FIG. 4C is a schematic cross-sectional view taken along line IVC-IVC of FIG. 4A with the mouthpiece in the biased state.
Figure 4D:
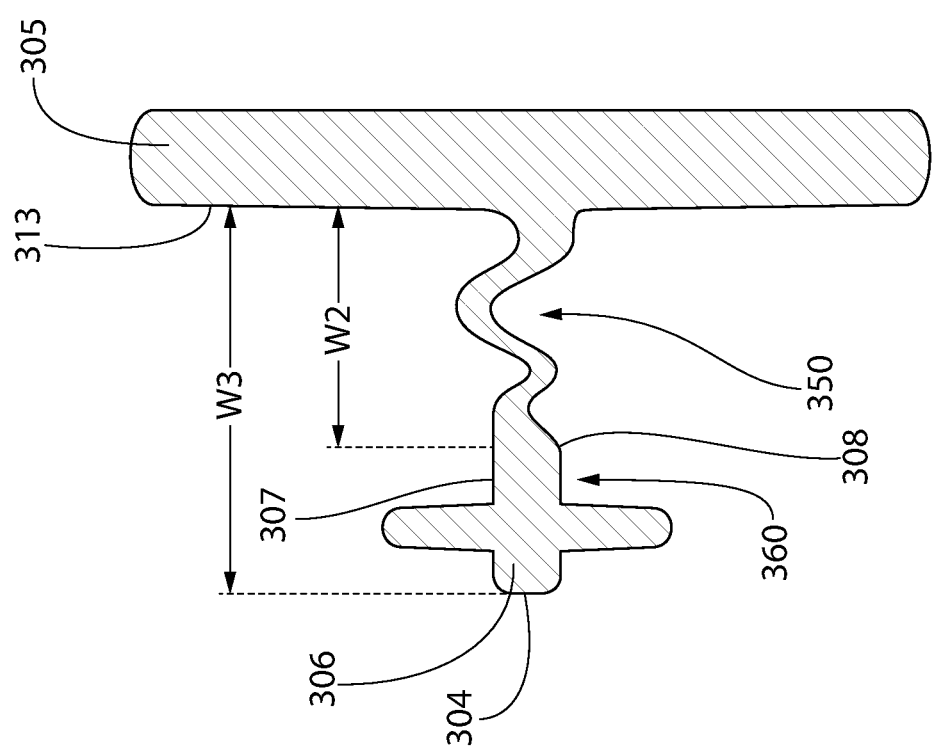
FIG. 4D is a schematic cross-sectional view taken along line IVC-IVC of FIG. 4A with the mouthpiece is in the flexed state.

As noted above, in the exemplified embodiment the collapsible region 250 has an accordion-like shape. As can be seen from FIGS. 3A and 3C, in the biased state the collapsible region 250 includes sections of material that are separated by gaps 251 having a first gap distance. As the force F is applied as indicated in FIGS. 3B and 3D, the gap distances become smaller as the material of the collapsible region 250 collapses/flexes into the gaps 251. This is what enables the mouthpiece 201 to have flexibility as discussed herein. Because the curved wall 205 is curved in the biased state, the curve simply becomes more pronounced in the flexed state as the collapsible region 250 collapses. As the mouthpiece 201 is altered from the biased state into the flexed state, the length of the collapsible region 250 measured along the axis A-A decreases. Specifically, the collapsible region 250 has a first length L1 measured in the direction of the axis A-A in the biased or non-collapsed state and a second length L2 measured in the direction of the axis A-A in the flexed or collapsed state, the first length L1 being greater than the second length L2. The lengths of the first and second non-collapsible regions 260, 270 remain the same in both the biased and flexed states. The first and second lengths L1, L2 are also the distance between the first and second non-collapsible regions 260, 270, which decreases when the mouthpiece 201 is altered from the biased state into the flexed state.

Referring to FIGS. 4A-4D, another embodiment of an oral treatment device 300 having increased flexibility will be described. The oral treatment device 300 is identical to the oral treatment device 100 described above except with regard to the features described specifically with regard to the oral treatment device 300. A similar numbering scheme will be used for the oral treatment device 300 as was used for the oral treatment device 100 except that the 300-series of numbers will be used. If a feature of the oral treatment device 300 is numbered but not described, the description of the similar feature with regard to the oral treatment device 100 applies. If a feature of the oral treatment device 300 is not numbered or described, the description of the similar feature of the oral treatment device 100 may apply.

The oral treatment device 300 generally comprises a mouthpiece 301 comprising a curved wall 305 and a bite platform 306. The curved wall 305 comprises a concave inner surface 313. The bite platform 306 extends from the concave inner surface 313 of the curved wall 305 and terminates in a distal end 304. In the exemplified embodiment the bite platform 306 extends substantially perpendicularly from the concave inner surface 313 of the curved wall 305, although the oral treatment device 300 is not to be so limited in all embodiments. The bite platform 304 comprises an upper surface 307 and a lower surface 308. Furthermore, similar to the discussion above, an electromagnetic radiation source 303 is coupled to the concave inner surface 313 of the curved wall 305. The electromagnetic radiation source 303 is operably coupled to a power source as described above in order to power the electromagnetic radiation source 303 to emit electromagnetic radiation (such as light) onto a user's teeth that are positioned adjacent to the electromagnetic radiation source 303 during use of the oral treatment device 300.

In order to permit the mouthpiece 301 to have an increased amount of flexibility, in the exemplified embodiment the bite platform 306 comprises at least one collapsible region 350. The collapsible region 350 of the bite platform 306 permits the mouthpiece 301 to be alterable between a biased state (FIG. 4A) in which the curved wall 305 has a first curvature and a flexed state (FIG. 4B) in which the curved wall 305 has a second curvature that is different than the first curvature. Specifically, pressure on opposing ends of the mouthpiece 301 causes the mouthpiece 301 to alter from the biased state to the flexed state. The mouthpiece 301 alters back into the biased state upon cessation of the force. The force can be applied by a user's hand squeezing the opposing ends of the mouthpiece 301, or by the orbicularis oris muscle of the mouth (or some other muscle within a user's mouth) that exerts pressure to mold or shape the now mouthpiece 301 to conform to the user's mouth. The distance D1 between the opposing ends of the curved wall 305 in the biased state (i.e., at the first curvature) is greater than a distance D2 between the opposing ends of the curved wall 305 in the flexed state (i.e., at the second curvature).

In this embodiment, the collapsible region 350 of the bite platform 306 extends continuously from a first end 341 of the bite platform 306 to a second end 342 of the bite platform 306. Thus, the collapsible region 350 of the bite platform 306 extends along an entirety of an axial length of the bite platform 306. However, in this embodiment the collapsible region 350 of the bite platform 306 does not extend from the concave inner surface 313 of the curved wall 305 all the way to the distal end 304 of the bite platform 306. Rather, the collapsible region 350 extends from the concave inner surface 313 of the curved wall 305 along a portion of the width of the bite platform 306 but not all the way to the distal end 304 of the bite platform 306. Thus, the collapsible region 350 extends along the entire length of the bite platform 306 and is adjacent to the concave inner surface 313 of the curved wall 305. In that regard, the bite platform 306 also includes a non-collapsible region 360 that extends from the distal end 304 of the bite platform 306 to the collapsible region 350 of the bite platform 306.

The upper and lower surfaces 307, 308 of the bite platform 306 are substantially flat and planar in the non-collapsible region 360. The upper and lower surfaces 307, 308 of the bite platform 306 are wavy or undulating in the collapsible region 350. As a result, the collapsible region 350 collapses as a force F is applied to the mouthpiece 301 as described above. The difference between the oral treatment device 300 and the oral treatment device 200 is primarily the location of the collapsible region 350, although it operates/functions in much the same way as the collapsible region 250 of the oral treatment device 200 described above. In this embodiment, the length of the collapsible region 350 and of the bite platform 306 is the same in both the biased and flexed states. However, the width of the collapsible region 350 (measured in the direction from the inner surface 313 of the curved wall 305 towards the distal end 304 of the bite platform 306) decreases when altering the mouthpiece 301 from the biased state to the flexed state. Specifically, the collapsible region 350 has a width W2 in the biased state and the bite platform 306 has a width W3 in the biased state. The collapsible region 350 has a width W4 in the flexed state and the bite platform 306 has a width W5 in the flexed state. The width W2 is greater than the width W4 and the width W3 is greater than the width W5.

Referring to FIGS. 5A-5D, another embodiment of an oral treatment device 400 having increased flexibility will be described. The oral treatment device 400 is identical to the oral treatment device 100 described above except with regard to the features described specifically with regard to the oral treatment device 400. A similar numbering scheme will be used for the oral treatment device 400 as was used for the oral treatment device 100 except that the 400-series of numbers will be used. If a feature of the oral treatment device 400 is numbered but not described, the description of the similar feature with regard to the oral treatment device 100 applies. If a feature of the oral treatment device 400 is not numbered or described, the description of the similar feature of the oral treatment device 100 may apply.

The oral treatment device 400 generally comprises a mouthpiece 401 comprising a curved wall 405 and a bite platform 406. The curved wall 405 comprises a concave inner surface 413. The bite platform 406 extends from the concave inner surface 413 of the curved wall 405 and terminates in a distal end 3404. In the exemplified embodiment the bite platform 406 extends substantially perpendicularly from the concave inner surface 413 of the curved wall 405, although the oral treatment device 400 is not to be so limited in all embodiments. The bite platform 404 comprises an upper surface 407 and a lower surface 408. Furthermore, similar to the discussion above, an electromagnetic radiation source 403 is coupled to the concave inner surface 413 of the curved wall 405. The electromagnetic radiation source 403 is operably coupled to a power source as described above in order to power the electromagnetic radiation source 403 to emit electromagnetic radiation (such as light) onto a user's teeth that are positioned adjacent to the electromagnetic radiation source 403 during use of the oral treatment device 400.

In order to permit the mouthpiece 401 to have an increased amount of flexibility, in the exemplified embodiment the bite platform 406 comprises at least one collapsible region 450. The collapsible region 450 of the bite platform 406 permits the mouthpiece 401 to be alterable between a biased state (FIG. 5A) in which the curved wall 405 has a first curvature and a flexed state (FIG. 5B) in which the curved wall 405 has a second curvature that is different than the first curvature. Specifically, pressure on opposing ends of the mouthpiece 401 causes the mouthpiece 401 to alter from the biased state to the flexed state. The mouthpiece 401 alters back into the biased state upon cessation of the force. The force can be applied by a user's hand squeezing the opposing ends of the mouthpiece 401, or by the orbicularis oris muscle of the mouth (or some other muscle within a user's mouth) that exerts pressure to mold or shape the now mouthpiece 401 to conform to the user's mouth. The distance D1 between the opposing ends of the curved wall 405 in the biased state (i.e., at the first curvature) is greater than the distance D2 between the opposing ends of the curved wall 405 in the flexed state (i.e., at the second curvature).

In this embodiment, the collapsible region 450 of the bite platform 406 is a portion of the bite platform 406 having a reduced thickness relative to a remainder of the bite platform 406. Specifically, in this embodiment the bite platform 406 comprises the collapsible region 450 and at least one non-collapsible region 460, 470. The non-collapsible regions 460, 470 have a first thickness TC1 measured from the lower surface 408 of the bite platform 406 to the upper surface 407 of the bite platform 406. The collapsible region 450 (or collapsible regions) of the bite platform 406 has a second thickness TC2 measured from the lower surface 408 of the bite platform 406 to the upper surface 407 of the bite platform 406. The second thickness TC2 is less than the first thickness TC1.

Figure 5A:
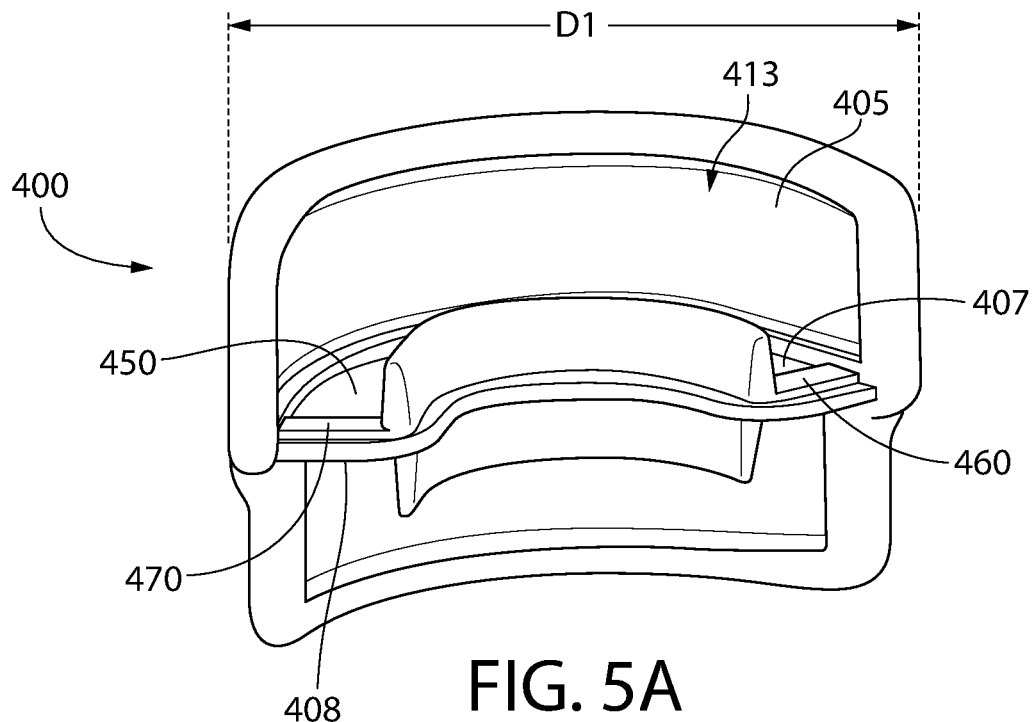
FIG. 5A is a front view of an oral treatment device including a mouthpiece and an electromagnetic radiation source in accordance with a fourth embodiment of the present invention, wherein the mouthpiece is in a biased state.
Figure 5B:
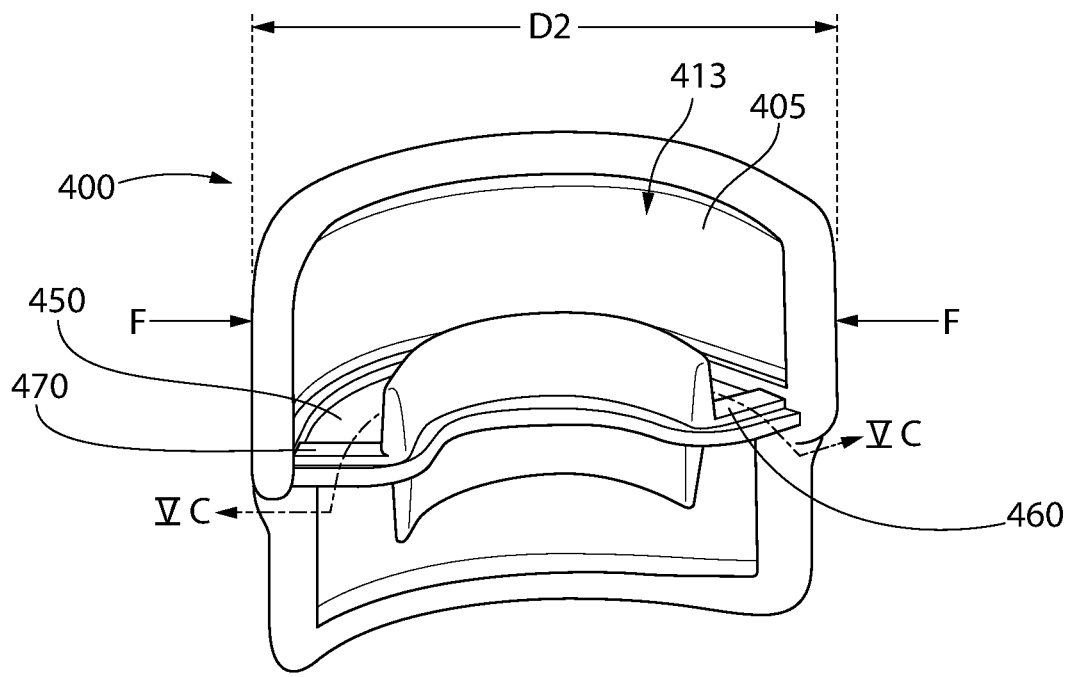
FIG. 5B is a front view of the oral treatment device of FIG. 5A wherein the mouthpiece is in a flexed state.
Figure 5C:
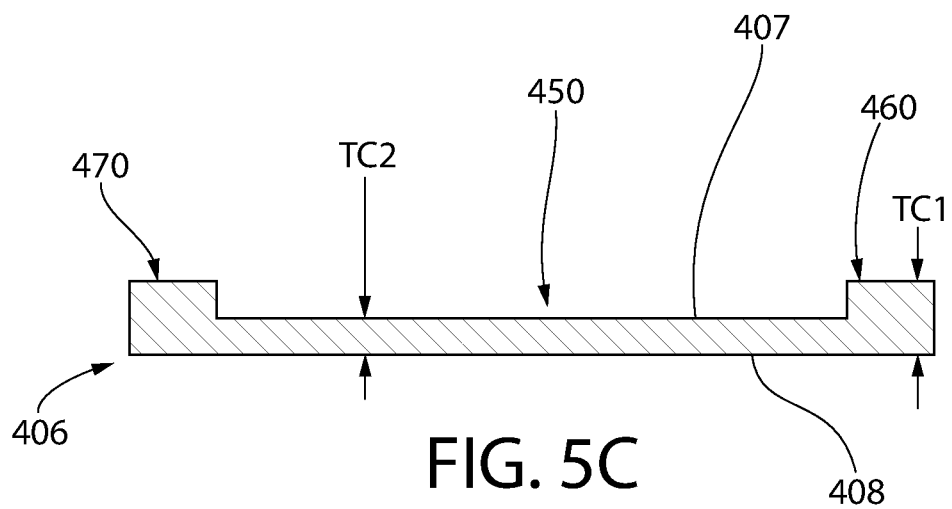
FIG. 5C is a schematic cross-sectional view taken along line VC-VC of a bite platform of the mouthpiece of FIG. 5A with the mouthpiece is in the biased state.
Figure 5D:
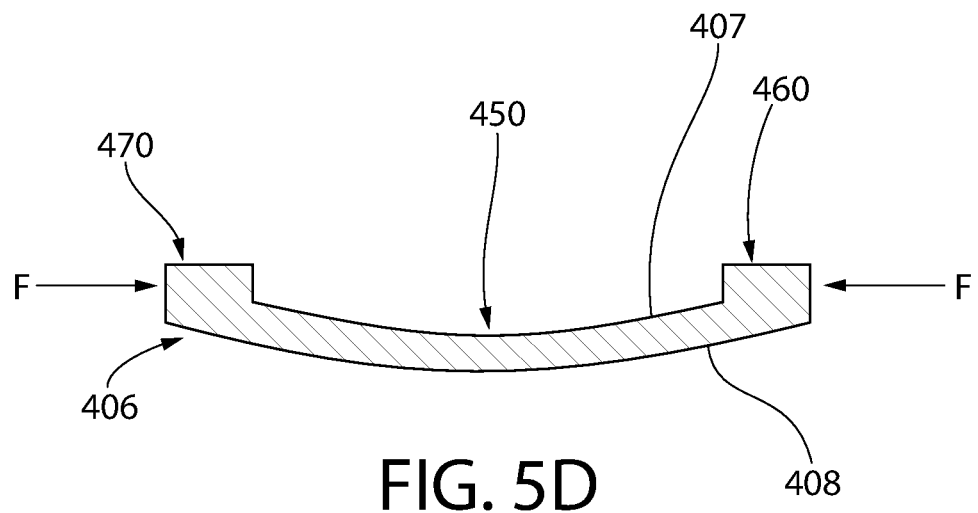
FIG. 5D is a schematic cross-sectional view taken along line VC-VC of the bite platform of the mouthpiece of FIG. 5A with the mouthpiece is in the flexed state.

The reduced thickness of the bite platform 406 in the collapsible region 450 permits the mouthpiece 401 to transition between the biased and flexed states. Specifically, when the force F is applied as discussed above, the collapsible region 450 of the bite platform 406 bends or curves, thereby enabling the curvature of the curved wall 405 to increase as discussed above. Thus, in the biased state the collapsible region 450 of the bite platform 406 has flat/planar upper and lower surfaces 407, 408. In the flexed state the collapsible region 450 curves so that one of the upper and lower surfaces 407, 408 is convex and the other of the upper and lower surfaces 407, 408 is concave. This is best illustrated in FIG. 5C (biased state) and FIG. 5D (flexed state), in which the upper surface 407 of the collapsible region 450 is concave and the lower surface 408 of the collapsible region 450 is convex, although of course the opposite may also occur.

As a result of the above disclosure, the mouthpieces 101, 201, 301, 401 described herein are designed to adjust manually to accommodate a broad range of user mouth shapes and sizes and different size sets of upper and lower teeth. The mouthpieces 101, 201, 301, 401 also ensure that the user's teeth remain in close proximity to the electromagnetic radiation source 103, 203, 303, 403 regardless of the user's mouth shape and size due to the flexibility of the device.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral treatment device comprising:
   a mouthpiece comprising a curved wall having a concave inner surface and a bite platform having an upper surface and a lower surface, the bite platform extending from the concave inner surface of the curved wall to a distal end; and
   an electromagnetic radiation source configured to emit electromagnetic radiation from the curved wall;
   wherein the upper and lower surfaces of the bite platform extend from the concave inner surface; and
   wherein the bite platform comprises at least one non-collapsible region and at least one collapsible region, the bite platform having a first thickness measured between the upper and lower surfaces of the bite platform in the at least one non-collapsible region and a second thickness measured between the upper and lower surfaces of the bite platform in the at least one collapsible region, the second thickness being less than the first thickness.

2. The oral treatment device according to claim 1 wherein the upper and lower surfaces of the bite platform are flat in the at least one non-collapsible region of the bite platform and wherein the upper and lower surfaces of the bite platform are wavy in the at least one collapsible region of the bite platform.

3. The oral treatment device according to claim 1 wherein the mouthpiece is alterable between: (1) a biased state in which the curved wall has a first curvature; and (2) a flexed state in which the curved wall has a second curvature that is greater than the first curvature, the mouthpiece altering from the biased state into the flexed state in response to application of force onto opposing ends of the mouthpiece in opposite directions, the mouthpiece altering from the flexed state into the biased state upon cessation of the force.

4. The oral treatment device according to claim 1 wherein the distal end of the bite platform is devoid of notches and extends continuously in a non-interrupted manner from a first end of the bite platform to a second end of the bite platform.

* * * * *